United States Patent
Meskens et al.

(10) Patent No.: US 11,679,267 B1
(45) Date of Patent: Jun. 20, 2023

(54) MEDICAL IMPLANT WITH STIMULATION LEAKAGE CURRENT BLOCKING

(71) Applicant: Cochlear Limited, Macquarie University (AU)

(72) Inventors: Werner Meskens, Opwijk (BE); Thomas Cooney, Redfern (AU); Guilhem Yvan Vavelin, Nice (FR)

(73) Assignee: Cochlear Limited, Macquarie University (AU)

( * ) Notice: Subject to any disclaimer, the term of this patent is extended or adjusted under 35 U.S.C. 154(b) by 187 days.

(21) Appl. No.: 17/141,907

(22) Filed: Jan. 5, 2021

Related U.S. Application Data

(60) Provisional application No. 62/981,727, filed on Feb. 26, 2020.

(51) Int. Cl.
| | | |
|---|---|---|
| A61N 1/378 | (2006.01) | |
| H02J 50/12 | (2016.01) | |
| A61N 1/372 | (2006.01) | |
| A61N 1/36 | (2006.01) | |
| A61N 1/362 | (2006.01) | |

(52) U.S. Cl.
CPC ....... *A61N 1/3787* (2013.01); *A61N 1/36038* (2017.08); *A61N 1/37223* (2013.01); *H02J 50/12* (2016.02); *A61N 1/362* (2013.01)

(58) Field of Classification Search
CPC .............. A61N 1/3787; A61N 1/36038; A61N 1/37223; A61N 1/362; H02J 50/12
See application file for complete search history.

(56) References Cited

U.S. PATENT DOCUMENTS

| | | | |
|---|---|---|---|
| 4,462,406 A | 7/1984 | Decote, Jr. | |
| 4,470,418 A | 9/1984 | Herscovici et al. | |
| 9,592,395 B2* | 3/2017 | Meskens | A61N 1/3787 |
| 2003/0204217 A1 | 10/2003 | Greatbatch | |
| 2004/0088012 A1 | 5/2004 | Kroll et al. | |
| 2008/0228270 A1 | 9/2008 | Dahlberg | |
| 2010/0145337 A1* | 6/2010 | Janna | A61B 17/1707 606/86 R |
| 2011/0251654 A1 | 10/2011 | Sivard et al. | |
| 2012/0116479 A1* | 5/2012 | Meskins | A61N 1/37217 607/57 |
| 2017/0154727 A1* | 6/2017 | Spina | H01L 23/645 |

FOREIGN PATENT DOCUMENTS

WO    WO 2012/063202 A2    5/2012

* cited by examiner

*Primary Examiner* — Catherine M Voorhees
(74) *Attorney, Agent, or Firm* — Knobbe, Martens, Olson & Bear LLP

(57) ABSTRACT

An apparatus includes implantable first circuitry configured to wirelessly receive power from a device external to the recipient's body, implantable second circuitry configured to provide stimulation signals to a portion of the recipient's body, and implantable third circuitry, at least a portion of the first circuitry and at least a portion of the third circuitry forming a series resonant tank circuit configured to capacitively couple the second circuitry to the first circuitry while galvanically isolating the second circuitry from the first circuitry, such that at least a portion of the electric power is transferred from the first circuitry to the second circuitry through the third circuitry whilst preventing stimulation currents.

28 Claims, 6 Drawing Sheets

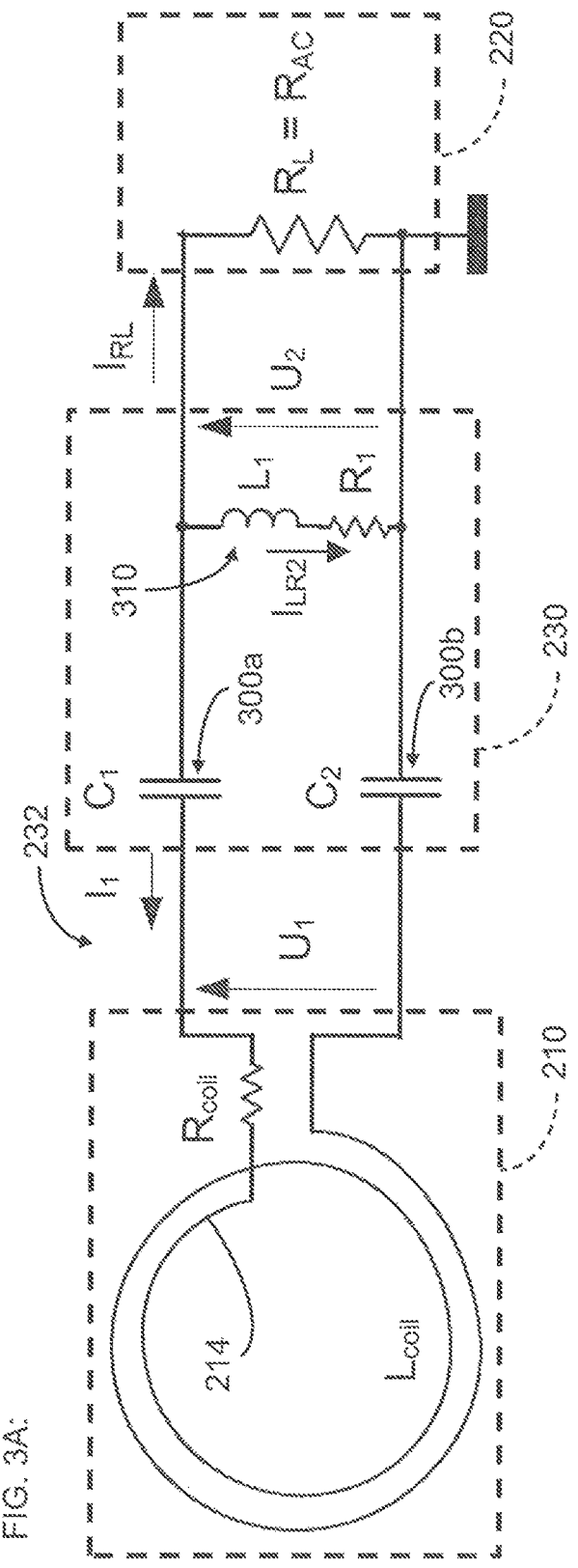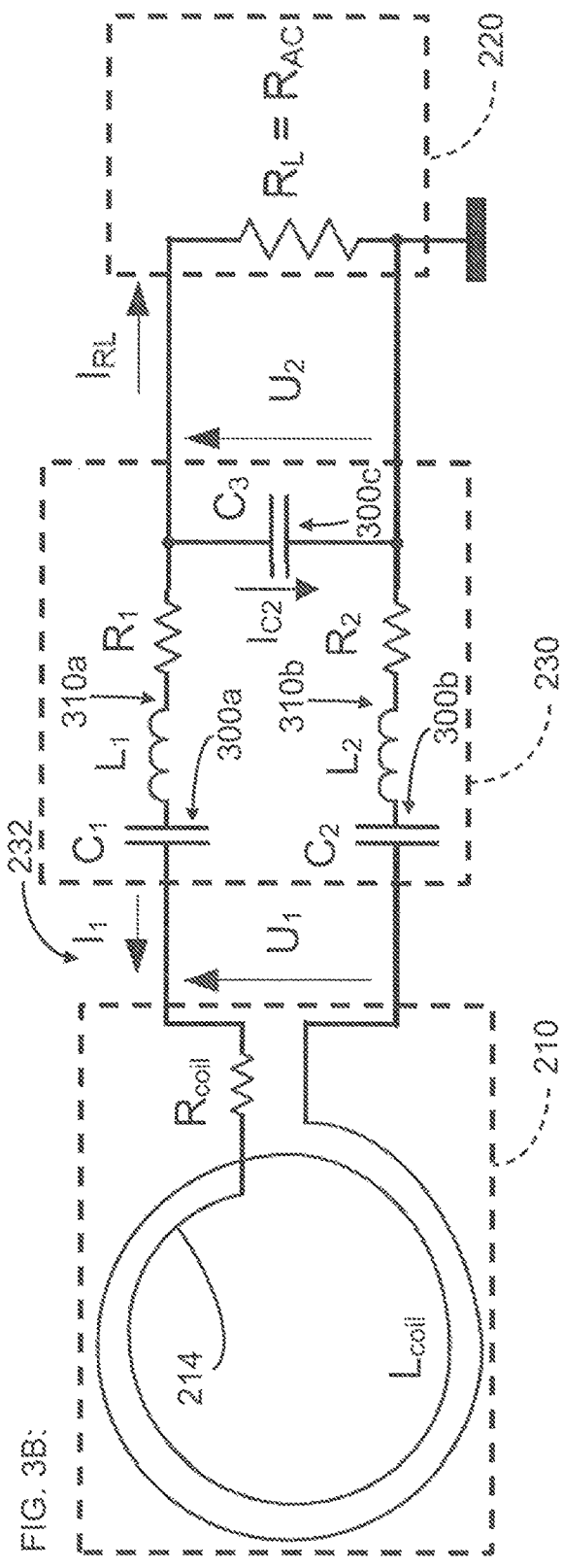
FIG. 3A.
FIG. 3B.

MEDICAL IMPLANT WITH STIMULATION LEAKAGE CURRENT BLOCKING

CLAIM OF PRIORITY

This application claims the benefit of priority to U.S. Provisional Appl. No. 62/981,727, filed Feb. 26, 2020, which is incorporated in its entirety by reference herein.

BACKGROUND

Field

The present application relates generally to systems and methods for facilitating wireless power transmission and distribution, and more specifically, for facilitating wireless power transmission between an external portion and an implanted portion of an implanted medical system and distribution of the power by the implanted portion.

Description of the Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect disclosed herein, an apparatus comprises first circuitry configured to be implanted on or within a recipient's body and to wirelessly receive power from a device external to the recipient's body. The apparatus further comprises second circuitry configured to be implanted on or within the recipient's body and to provide stimulation signals to a portion of the recipient's body. The apparatus further comprises third circuitry configured to be implanted on or within the recipient's body, at least a portion of the first circuitry and at least a portion of the third circuitry forming a series resonant tank circuit configured to capacitively couple the second circuitry to the first circuitry while galvanically isolating the second circuitry from the first circuitry, such that at least a portion of the electric power is transferred from the first circuitry through the third circuitry to the second circuitry.

In another aspect disclosed herein, a method comprises receiving electric power and/or data signals using circuitry implanted on or within a recipient's body. The electric power and/or data signals are received via a magnetic induction link between the circuitry and a device external to the recipient's body. The method further comprises transferring at least a portion of the received electrical power and/or data signals to an implanted stimulator unit configured to provide stimulation signals to a portion of the recipient's body at a stimulation pulse rate. The transferred electrical power and/or data signals have a first frequency above the stimulation pulse rate. The method further comprises decoupling electrical signals from the stimulator unit from reaching the circuitry, the decoupled electrical signals having a second frequency in a range at or below the stimulation pulse rate.

In another aspect disclosed herein, an apparatus comprises a first electric portion implanted within the recipient's body. The first electric portion comprises a magnetic induction coil configured to wirelessly receive power and/or data signals from a device external to the recipient's body. The apparatus further comprises a second electric portion implanted within the recipient's body. The second electric portion is configured to generate electrical stimulation signals to a portion of the recipient's body. The second electrical portion is capacitively coupled to the first electrical portion and is configured to receive at least a portion of the power and/or data signals from the first electric portion. The second electrical portion comprises a plurality of capacitors and at least one inductor, and the plurality of capacitors and the at least one inductor are configured to provide an isolation impedance between the first and second electrical portions sufficient to block the electrical stimulation signals from the first electric portion.

BRIEF DESCRIPTION OF THE DRAWINGS

Implementations are described herein in conjunction with the accompanying drawings, in which:

FIGS. 3A-3D schematically illustrate various examples of the series resonant tank circuit in accordance with certain implementations described herein.

DETAILED DESCRIPTION

Figure 1:
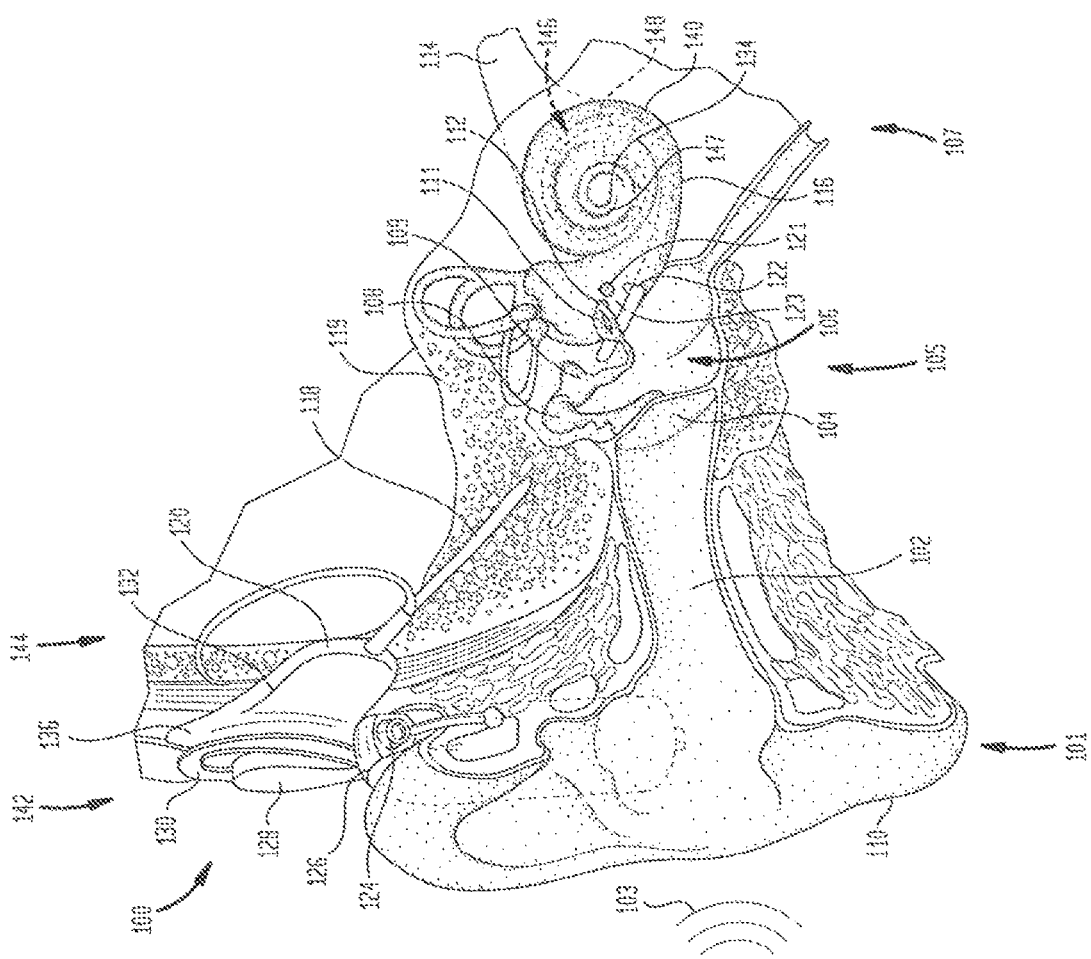
FIG. 1 is a perspective view of an example cochlear implant auditory prosthesis implanted in a recipient in accordance with certain implementations described herein.

Certain implementations described herein provides an implantable medical device (e.g., cochlear implant system) that includes an isolation barrier to avoid a stimulation current loop of biphasic stimulation signals flowing between the stimulation electrodes and other portions of the implantable medical device. For example, the implantable medical device can include a series resonant tank circuit configured to capacitively couple the stimulation assembly to a radiofrequency (RF) coil assembly configured to wirelessly receive power from an external device while galvanically isolating the stimulation assembly from the RF coil assembly. Certain implementations described herein are configured to virtually increase the coil inductance of the RF coil assembly while keeping the number of turns of the RF coil assembly low (e.g., two to four turns), to keep a predetermined voltage transfer ratio, and/or to provide comparable AC leakage protection by utilizing series capacitors with relatively low capacitance (e.g., less than 10 nF).

The teachings detailed herein are applicable, in at least some implementations, to any type of implantable medical device (e.g., implantable sensory prostheses) comprising a first portion (e.g., external to a recipient) and a second portion (e.g., implanted on or within the recipient), the first portion configured to wirelessly transmit power to the second portion. For example, the implantable medical device can comprise an auditory prosthesis system utilizing an external sound processor configured to transcutaneously provide power to an implanted assembly (e.g., comprising an actuator). In certain such examples, the external sound processor is further configured to transcutaneously provide data (e.g., control signals) to the implanted assembly that responds to the data by generating stimulation signals that are perceived by the recipient as sounds. Examples of auditory prosthesis systems compatible with certain implementations described herein include but are not limited to: electro-acoustic electrical/acoustic systems, cochlear implant devices, implantable hearing aid devices, middle ear implant devices, Direct Acoustic Cochlear Implant (DACI), middle ear transducer (MET), electro-acoustic implant devices, other types of auditory prosthesis devices, and/or combinations or variations thereof, or any other suitable hearing prosthesis system with or without one or more external components. Implementations can include any type of medical device that can utilize the teachings detailed herein and/or variations thereof.

Merely for ease of description, apparatus and methods disclosed herein are primarily described with reference to an illustrative medical device, namely a cochlear implant. However, the teachings detailed herein and/or variations thereof may also be used with a variety of other medical devices that provide a wide range of therapeutic benefits to recipients, patients, or other users. In some implementations, the teachings detailed herein and/or variations thereof can be utilized in other types of implantable medical devices beyond auditory prostheses. For example, apparatus and methods disclosed herein and/or variations thereof may also be used with one or more of the following: vestibular devices (e.g., vestibular implants); visual devices (e.g., bionic eyes); visual prostheses (e.g., retinal implants); sensors; cardiac pacemakers; drug delivery systems; defibrillators; functional electrical stimulation devices; catheters; brain implants; seizure devices (e.g., devices for monitoring and/or treating epileptic events); sleep apnea devices; electroporation; pain relief devices; etc. The concepts described herein and/or variations thereof can be applied to any of a variety of implantable medical devices comprising an implanted component configured to use magnetic induction to receive power (e.g., transcutaneously) from an external component and to store at least a portion of the power in at least one power storage device (e.g., battery). The implanted component can also be configured to receive control signals from the external component (e.g., transcutaneously) and/or to transmit sensor signals to the external component (e.g., transcutaneously) while receiving power from the external component. In still other implementations, the teachings detailed herein and/or variations thereof can be utilized in other types of systems beyond medical devices utilizing magnetic induction for wireless power transfer. For example, such other systems can include one or more of the following: consumer products (e.g., smartphones; "internet-of-things" or IoT devices) and electric vehicles (e.g., automobiles).

FIG. 1 is a perspective view of an example cochlear implant auditory prosthesis 100 implanted in a recipient in accordance with certain implementations described herein. The example auditory prosthesis 100 is shown in FIG. 1 as comprising an implanted stimulator unit 120 (e.g., an actuator) and an external microphone assembly 124 (e.g., a partially implantable cochlear implant). An example auditory prosthesis 100 (e.g., a totally implantable cochlear implant) in accordance with certain implementations described herein can replace the external microphone assembly 124 shown in FIG. 1 with a subcutaneously implantable assembly comprising an acoustic transducer (e.g., microphone), as described more fully herein.

As shown in FIG. 1, the recipient normally has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within the cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more input elements/devices for receiving input signals at a sound processing unit 126. The one or more input elements/devices can include one or more sound input elements (e.g., one or more external microphones 124) for detecting sound and/or one or more auxiliary input devices (not shown in FIG. 1)(e.g., audio ports, such as a Direct Audio Input (DAI); data ports, such as a Universal Serial Bus (USB) port; cable ports, etc.). In the example of FIG. 1, the sound processing unit 126 is a behind-the-ear (BTE) sound processing unit configured to be attached to, and worn adjacent to, the recipient's ear. However, in certain other implementations, the sound processing unit 126 has other arrangements, such as by an OTE processing unit (e.g., a component having a generally cylindrical shape and which is configured to be magnetically coupled to the recipient's head), a mini or micro-BTE unit, an in-the-canal unit that is configured to be located in the recipient's ear canal, a body-worn sound processing unit, etc.

The sound processing unit 126 of certain implementations includes a power source (not shown in FIG. 1)(e.g., battery), a processing module (not shown in FIG. 1)(e.g., comprising one or more digital signal processors (DSPs), one or more microcontroller cores, one or more application-specific integrated circuits (ASICs), firmware, software, etc. arranged to perform signal processing operations), and an external transmitter unit 128. In the illustrative implementation of FIG. 1, the external transmitter unit 128 comprises circuitry that includes at least one external inductive communication coil 130 (e.g., a wire antenna coil comprising multiple turns of electrically insulated single-strand or multi-strand platinum or gold wire). The external transmitter unit 128 also generally comprises a magnet (not shown in FIG. 1) secured directly or indirectly to the at least one external inductive communication coil 130. The at least one external inductive communication coil 130 of the external transmitter unit 128 is part of an inductive radio frequency (RF) communication link with the internal component 144. The sound processing unit 126 processes the signals from the input elements/devices (e.g., microphone 124 that is positioned externally to the recipient's body, in the depicted implementation of FIG. 1, by the recipient's auricle 110). The sound processing unit 126 generates encoded signals, sometimes referred to herein as encoded data signals, which are provided to the external transmitter unit 128 (e.g., via a cable). As will be appreciated, the sound processing unit 126 can utilize digital processing techniques to provide frequency shaping, amplification, compression, and other signal conditioning, including conditioning based on recipient-specific fitting parameters.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate stimulation assembly 118. In some implementations, the internal receiver unit 132 and the stimulator unit 120 are hermetically sealed within a biocompatible housing, sometimes collectively referred to as a stimulator/receiver unit. The internal receiver unit 132 comprises at least one internal inductive communication coil 136 (e.g., a wire antenna coil comprising multiple turns of electrically insulated single-strand or multi-strand platinum or gold wire), and generally, a magnet (not shown in FIG. 1) fixed relative to the at least one internal inductive communication coil 136. The at least one internal inductive communication coil 136 receives power and/or data signals from the at least one external inductive communication coil 130 via a transcutaneous energy transfer link (e.g., an inductive RF link). The stimulator unit 120 generates stimulation signals (e.g., electrical stimulation signals; optical stimulation signals) based on the data signals, and the stimulation signals are delivered to the recipient via the elongate stimulation assembly 118.

The elongate stimulation assembly 118 has a proximal end connected to the stimulator unit 120, and a distal end implanted in the cochlea 140. The stimulation assembly 118 extends from the stimulator unit 120 to the cochlea 140 through the mastoid bone 119. In some implementations, the stimulation assembly 118 can be implanted at least in the basal region 116, and sometimes further. For example, the stimulation assembly 118 can extend towards an apical end of the cochlea 140, referred to as the cochlea apex 134. In certain circumstances, the stimulation assembly 118 can be inserted into the cochlea 140 via a cochleostomy 122. In other circumstances, a cochleostomy can be formed through the round window 121, the oval window 112, the promontory 123, or through an apical turn 147 of the cochlea 140.

The elongate stimulation assembly 118 comprises a longitudinally aligned and distally extending array 146 (e.g., electrode array; contact array) of stimulation elements 148 (e.g., electrical electrodes; electrical contacts; optical emitters; optical contacts). The stimulation elements 148 are longitudinally spaced from one another along a length of the elongate body of the stimulation assembly 118. For example, the stimulation assembly 118 can comprise an array 146 comprising twenty-two (22) stimulation elements 148 that are configured to deliver stimulation to the cochlea 140. Although the array 146 of stimulation elements 148 can be disposed on the stimulation assembly 118, in most practical applications, the array 146 is integrated into the stimulation assembly 118 (e.g., the stimulation elements 148 of the array 146 are disposed in the stimulation assembly 118). As noted, the stimulator unit 120 generates stimulation signals (e.g., electrical signals; optical signals) which are applied by the stimulation elements 148 to the cochlea 140, thereby stimulating the auditory nerve 114.

While FIG. 1 schematically illustrates an auditory prosthesis 100 utilizing an external component 142 comprising an external microphone 124, an external sound processing unit 126, and an external power source, in certain other implementations, one or more of the microphone 124, sound processing unit 126, and power source are implantable on or within the recipient (e.g., within the internal component 144). For example, the auditory prosthesis 100 can have each of the microphone 124, sound processing unit 126, and power source implantable on or within the recipient (e.g., encapsulated within a biocompatible assembly located subcutaneously), and can be referred to as a totally implantable cochlear implant ("TICI"). For another example, the auditory prosthesis 100 can have most components of the cochlear implant (e.g., excluding the microphone, which can be an in-the-ear-canal microphone) implantable on or within the recipient, and can be referred to as a mostly implantable cochlear implant ("MICI").

Figure 2A:
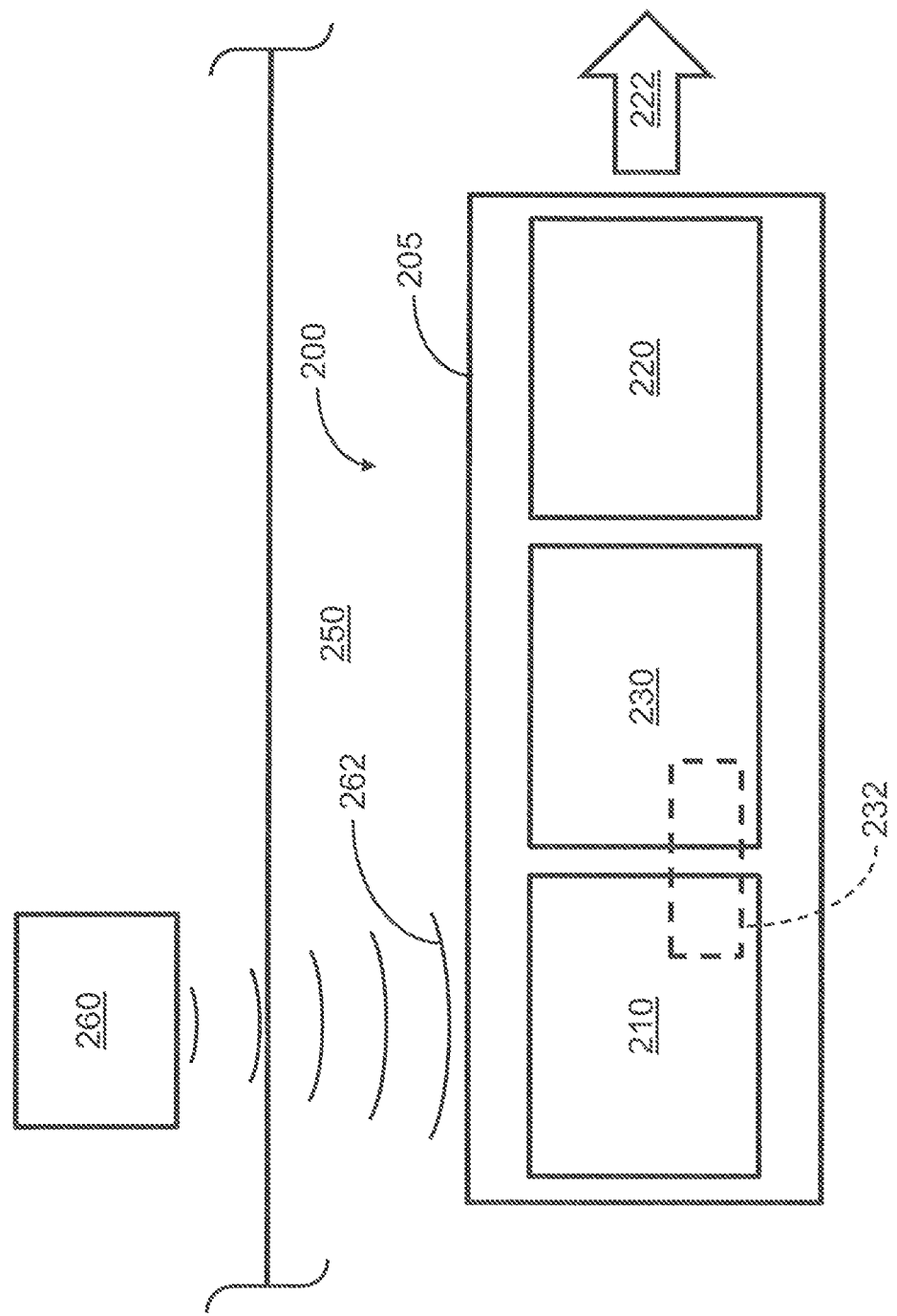
FIGS. 2A and 2B schematically illustrate an example apparatus in accordance with certain implementations described herein.
Figure 2B:
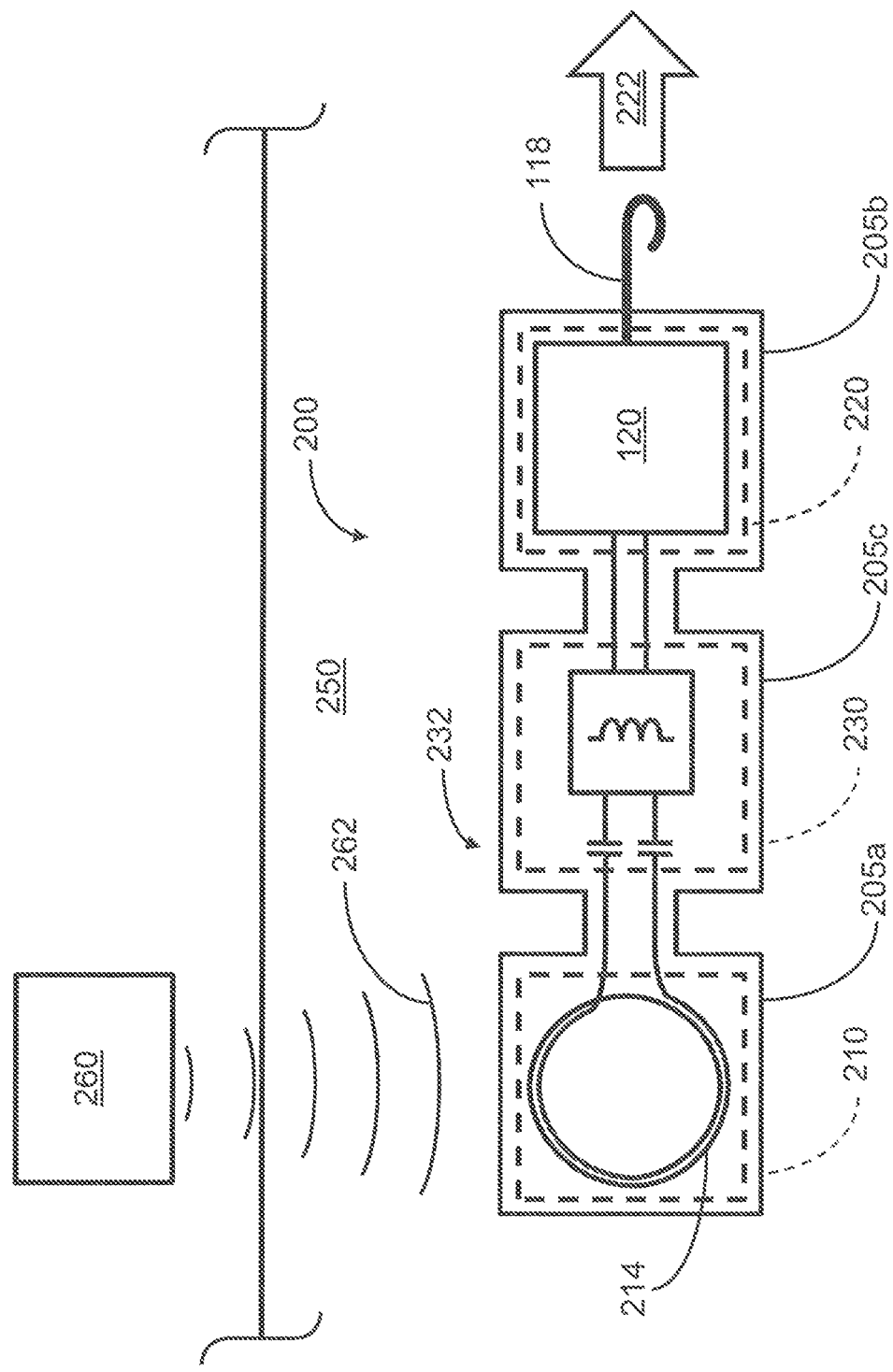

FIGS. 2A and 2B schematically illustrates an example apparatus 200 in accordance with certain implementations described herein. The apparatus 200 comprises first circuitry 210 configured to be implanted on or within a recipient's body 250 and to wirelessly receive power 262 from a device 260 external to the recipient's body 250. The apparatus 200 further comprises second circuitry 220 configured to be implanted on or within the recipient's body 250 and to provide stimulation signals 222 to a portion of the recipient's body 250. The apparatus 200 further comprises third circuitry 230 configured to be implanted on or within the recipient's body 250, at least a portion of the first circuitry 210 and at least a portion of the third circuitry 230 forming a series resonant tank circuit 232 configured to capacitively couple the second circuitry 220 to the first circuitry 210 while galvanically isolating the second circuitry 220 from the first circuitry 210, such that at least a portion of the electric power is transferred from the first circuitry 210 through the third circuitry 230 to the second circuitry 220.

In certain implementations, the apparatus 200 is an implanted portion of a medical system (e.g., a portion of the medical system that is implanted on or within the recipient) and the device 260 from which the apparatus 200 wirelessly receives the power 262 comprises an external portion of the medical system (e.g., a portion worn by the recipient; a portion that is configured to be repeatedly attached and detached from the apparatus 200 and/or the recipient). For example, the device 260 can comprise an external portion (e.g., a sound processing unit 126) of an auditory prosthesis 100 (e.g., a cochlear implant system) and the apparatus 200 can comprise an implanted stimulator unit 120. In certain implementations, the first circuitry 210 is a first electrical portion implanted within the recipient's body (e.g., as a part of the implanted portion of the medical system) and the second circuitry 220 is a second electrical portion implanted within the recipient's body (e.g., as a part of the implanted portion of the medial system). While certain implementations are described herein as having the third circuitry 230 as a separate component from the first circuitry 210 and the second circuitry 220, in certain implementations, the third circuitry 230 can be integral with the first circuitry 210 (e.g., as a part of the first electrical portion) and/or integral with the second circuitry 220 (e.g., as a part of the second electrical portion).

In certain implementations, the apparatus 200 comprises at least one housing 205 configured to be implanted on or within the recipient's body 250, and the first circuitry 210, the second circuitry 220, and the third circuitry 230 are within the at least one housing 205. In certain such implementations, the at least one housing 205 comprises at least one biocompatible material (e.g., polymer; PEEK; silicone; titanium; titanium alloy; ceramic) and is configured to be at least partially implanted on or within the recipient (e.g., a region within the at least one housing 205 is hermetically sealed from a region outside the at least one housing 205). As schematically illustrated by FIG. 2B, the at least one housing 205 comprises a first housing portion 205a configured to contain the first circuitry 210 (e.g., an elastic biocompatible silicone layer/disk), a second housing portion 205b configured to contain the second circuitry 220 (e.g., a first portion of a titanium implant body), and a third housing portion 205c (e.g., a second portion of the titanium implant body) configured to contain the third circuitry 230. The first, second, and third housing portions 205a-c can be configured to allow electrical conduits (e.g., wires) to provide electrical communication among the first circuitry 210, second circuitry 220, and third circuitry 230.

Besides containing the first circuitry 210, the second circuitry 220, and the third circuitry 230, the at least one housing 205 of certain implementations is configured to further contain at least one of: communication circuitry (e.g., magnetic inductive RF data transfer circuitry; at least one antenna configured to be operationally coupled to a corresponding at least one antenna of the external device 260) configured to communicate data signals to and/or from the external device 260; processing circuitry configured to process data signals from the external device 260; a magnetic material configured to interact with a magnet of the external device 260 to create an attractive magnetic force that adheres the external device 260 to the recipient's body 250 (e.g., holds the external device 260 in an operative position relative to the apparatus 200). For example, for an auditory prosthesis 100, the communication circuitry can be configured to receive data signals generated by a microphone 124 and transmitted to the apparatus 200 by a sound processing unit 126, and the processing circuitry can be configured to process the received data signals (e.g., utilizing digital processing techniques for frequency shaping, amplification, compression, and/or other signal conditioning, including conditioning based on recipient-specific fitting parameters). The second circuitry 220 can be configured to respond to the processed data signals by generating the stimulation signals 222 that are provided to a portion of the recipient's body 250 (e.g., to create a hearing percept).

In certain implementations, the first circuitry 210 comprises at least one electrically conductive power transfer coil 214 configured to be operationally coupled by magnetic induction to at least one corresponding electrically conductive power transfer coil of the external device 260. For example, the at least one power transfer coil 214 can comprise an implant RF coil comprising an electrically conductive conduit (e.g., platinum wire; doped gold wire; conductive trace on a printed circuit board). The at least one power transfer coil 214 is configured to generate electric power in response to a time-varying magnetic field generated by the at least one power transfer coil of the external device 260. For example, the time-varying magnetic field and the electric power can have a frequency in a range of 100 kHz to 100 MHz (e.g., 5 MHz; 6.78 MHz; less than 10 MHz; less than 15 MHz; less than 30 MHz; less than 50 MHz). In certain implementations in which the apparatus 200 comprises an implanted portion of a medical system, the power transfer is in a range of 0.5 mW to 5000 mW. In certain other implementations, the power transfer is in a range of 1 W to 2 kW (e.g., for an apparatus 200 comprising a consumer device, examples of which include but are not limited to smartphone chargers and kitchen appliances, and/or an "internet-of-things" or IoT device) or in a range of 2 kW to 100 kW (e.g., for an apparatus comprising a vehicle).

In certain implementations, the first circuitry 210 further comprises at least one magnetic induction coil configured to transmit data signals between the first circuitry 210 and the device 260 external to the recipient's body. For example, the external device 260 can comprise at least one microphone configured to generate data signals that are transmitted from the device 260 to the first circuitry 210 (e.g., for a cochlear implant system having an external microphone). For another example, the first circuitry 210 can comprise at least one microphone configured to provide the first circuitry 210 with auditory data signals (e.g., for a totally implantable cochlear implant system).

In certain implementations in which the apparatus 200 is an implanted portion of a medical system, the second circuitry 220 is configured to provide stimulation signals 222 to a portion of the recipient's body 250. For example, for a cochlear implant auditory prosthesis 100 (see, e.g., FIG. 1), the second circuitry 220 can comprise an implanted stimulator unit 120 in operative communication with a stimulation assembly 118 (e.g., comprising an elongate array 146 of stimulation elements 148) and configured to generate the stimulation signals 222 (e.g., electrical stimulation signals; optical stimulation signals) in response to received data signals and to deliver the stimulation signals 222 to the recipient (e.g., to the cochlea 140 to create a hearing percept) via the elongate stimulation assembly 118. For another example, for an implanted visual prosthesis (e.g., retinal prosthesis), the second circuit 220 can comprise an array of stimulation elements configured to generate the stimulation signals 222 in response to received data signals and to deliver the stimulation signals 222 to the recipient (e.g., to the optic nerve or other portion of the recipient's vision system to create a vision percept). In still another example, for an implanted cardiac pacemaker, the second circuit 220 can comprise one or more stimulation elements (e.g., electrodes) configured to generate the stimulation signals 222 in response to received data signals and to deliver the stimulation signals 222 to the recipient (e.g., to selected portions of the heart to modify and/or control the heart's operation).

FIGS. 3A-3D schematically illustrate various examples of the series resonant tank circuit 232 in accordance with certain implementations described herein. In each of FIGS. 3A-3D, the example series resonant tank circuit 232 is formed by at least a portion of the first circuitry 210 (e.g., the power transfer coil 214) and at least a portion of the third circuitry 230. The portion of the third circuitry 230 comprises at least one capacitor 300 and at least one inductor 310 and is in electrical communication with the power transfer coil 214 (e.g., having an inductance $L_{coil}$ and a resistance $R_{coil}$) of the first circuitry 210. In certain implementations, the inductance of the series resonant tank circuit 232 is distributed among the portion of the first circuitry 210 and the portion of the third circuitry 230. In certain implementations, the third circuitry 230 is further configured to allow electrical currents operating in a frequency range (e.g., pulsed electrical currents having a pulse rate) greater than or equal to a predetermined value (e.g., 20 kHz) to transmit through the third circuitry 230 from the second circuitry 220 to the first circuitry 210 while preventing pulsed electrical currents having a pulse rate less than the predetermined value from transmitting through the third circuitry 230 from the first circuitry 210 to the second circuitry 220. These pulsed electrical currents can be captured from electrical stimulation currents flowing from the tissue inside the first circuitry 210 in absence of the preventative third circuitry 230. In certain implementations, the at least one capacitor 300 and the at least one inductor 310 of the third circuitry 230 are configured to provide an isolation impedance between the first circuitry 210 and the second circuitry 220 that is sufficient to block the stimulation signals 222 from the first circuitry 210 (e.g., at a stimulation rate in a frequency range less than or equal to 20 kHz). In certain such implementations, the at least one inductor 310 is configured to increase the isolation impedance between the first circuitry 210 and the second circuitry 220 to be greater than an isolation impedance between the first circuitry 210 and the second circuitry 220 without the at least one inductor 310.

For the example series resonant tank circuit 232 schematically illustrated in FIG. 3A (which can be referred to as "inductor loaded"), the at least one capacitor 300 comprises at least one first capacitor 300a having a first capacitance $C_1$ and at least one second capacitor 300b having a second capacitance $C_2$ that is substantially equal to the first capacitance $C_1$. The at least one inductor 310 comprises an inductor having a first inductance $L_1$ and a first resistance $R_1$ (e.g., inductor loss) and is in parallel with a load having a resistance $R_L$ due to the second circuitry 220. The at least one first capacitor 300a is in series with a first node of the at least one inductor 310 and the at least one second capacitor 300b is in series with a second node of the at least one inductor 310, the second node different from the first node. For example, the first capacitance $C_1$ can be in a range of 100 pF to 1 nF and the first inductance $L_1$ can be in a range of 0.2 micro Henry to 20 micro Henry.

In certain implementations in accordance with the third circuitry 230 of FIG. 3A, the first and second capacitances $C_1$, $C_2$ are sufficiently low (e.g., in a range of 100 pF to 1 nF) such that, during operation, the at least one capacitor 300 is a blocking capacitor for DC signals and stimulation AC signals. The values of the first and second capacitances $C_1$, $C_2$ and the first inductance $L_1$ can be set such that the power transfer coil 214 is basically in series resonance (e.g., unloaded) at a predetermined frequency (e.g., 5 MHz; 6.78 MHz). In certain implementations, the voltage $U_2$ over the at least one inductor 310 is boosted by the Q of the series resonant tank circuit 232. In certain implementations, the coil inductance $L_{coil}$ can be seen as a voltage source with mutual inductance $M_{21}$ that is much less than the first inductance $L_1$.

For the example series resonant tank circuit 232 schematically illustrated in FIG. 3B (which can be referred to as "capacitor loaded"), the at least one capacitor 300 comprises at least one first capacitor 300a having a first capacitance $C_1$, at least one second capacitor 300b having a second capacitance $C_2$ that is substantially equal to the first capacitance $C_1$, and at least one third capacitor 300c having a third capacitance $C_3$ in parallel with a load having a resistance $R_L$ due to the second circuitry 220. The at least one inductor 310 comprises at least one first inductor 310a having a first inductance $L_1$ and a first resistance $R_1$ (e.g., inductor loss) and at least one second inductor 310b having a second inductance $L_2$ that is substantially equal to the first inductance $L_1$ and a second resistance $R_2$ (e.g., inductor loss) that can be substantially equal to the first resistance $R_1$. The at least one first capacitor 300a is in series with the at least one first inductor 310a and with a first node of the at least one third capacitor 300c. The at least one second capacitor 300b is in series with the at least one second inductor 310b and with a second node of the at least one third capacitor 300c, the second node different from the first node.

In certain implementations in accordance with the third circuitry 230 of FIG. 3B, the first and second capacitances $C_1$, $C_2$ are sufficiently low (e.g., in a range of 100 pF to 1 nF) such that, during operation, the at least one capacitor 300 is a blocking capacitor for DC signals and stimulation AC signals. The values of the first, second, and third capacitances $C_1$, $C_2$, $C_3$ and the first and second inductances $L_1$, $L_2$ can be set such that the power transfer coil 214 is basically in series resonance (e.g., unloaded) at a predetermined frequency (e.g., 5 MHz; 6.78 MHz). In certain implementations, the voltages $U_1$, $U_2$ over the at least one capacitor 300 are boosted by the Q of the series resonant tank circuit 232. In certain implementations, the coil inductance $L_{coil}$ can be seen as a voltage source with mutual inductance $M_{21}$ that is much less than the first and second inductances $L_1$, $L_2$. The at least one capacitor 300 of certain implementations operates as a voltage divider. In certain implementations, increasing the first and second inductances $L_1$, $L_2$ can be used to set the values of the first, second, and third capacitances $C_1$, $C_2$, $C_3$ to practical values.

Figure 3C:
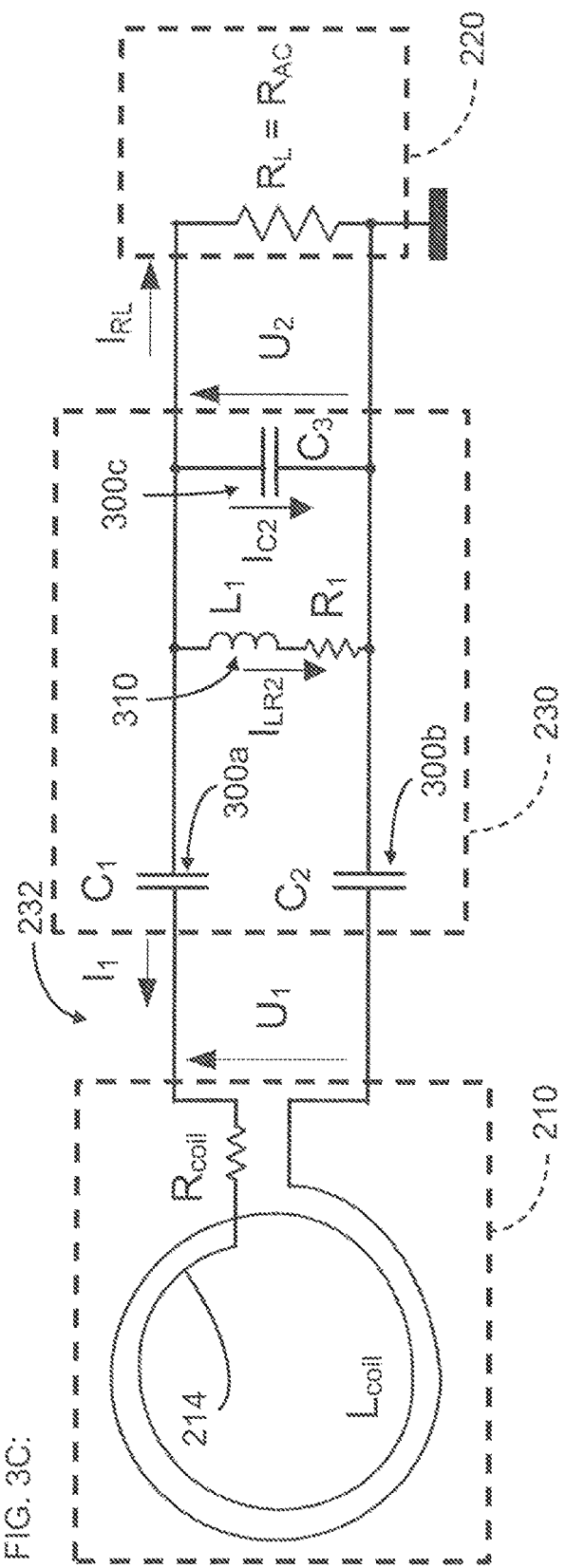

The example series resonant tank circuit 232 schematically illustrated in FIG. 3C (which can be referred to as "inductor loaded with detuning capacitor") is similar to the "inductor loaded" example series resonant tank circuit 232 schematically illustrated in FIG. 3A. The at least one capacitor 300 comprises at least one first capacitor 300a having a first capacitance $C_1$ and at least one second capacitor 300b having a second capacitance $C_2$ that is substantially equal to the first capacitance $C_1$. The at least one inductor 310 comprises an inductor having a first inductance $L_1$ and a first resistance $R_1$ (e.g., inductor loss) and is in parallel with a load having a resistance $R_L$ due to the second circuitry 220. The at least one first capacitor 300a is in series with a first node of the at least one inductor 310 and the at least one second capacitor 300b is in series with a second node of the at least one inductor 310, the second node different from the first node. For example, the first capacitance $C_1$ can be in a range of 100 pF to 1 nF and the first inductance $L_1$ can be in a range of 0.2 micro Henry to 20 micro Henry. The at least one capacitor 300 further comprises a third capacitor 300c having a third capacitance $C_3$ in parallel with the at least one inductor 310.

Figure 3D:
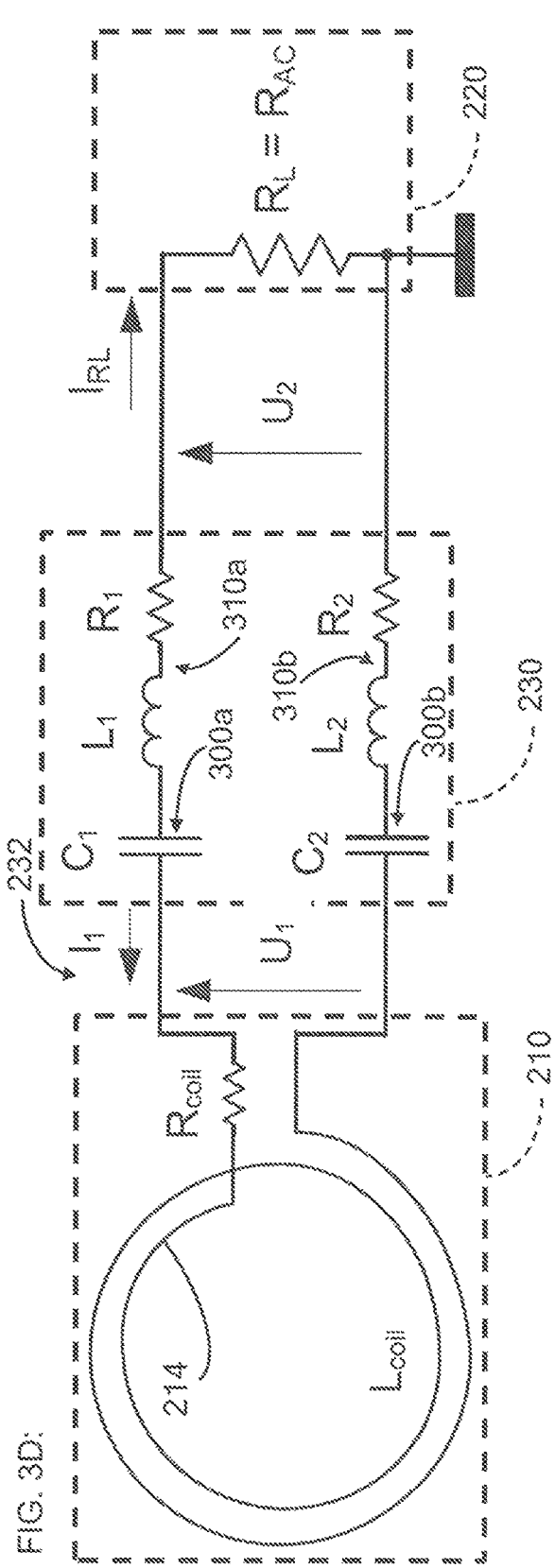

The example series resonant tank circuit 232 schematically illustrated in FIG. 3D (which can be referred to as "low resistor loaded") is similar to the "capacitor loaded" example series resonant tank circuit 232 schematically illustrated in FIG. 3B, but without the at least one third capacitor (e.g., third capacitance $C_3$ equal to infinity). The at least one capacitor 300 comprises at least one first capacitor 300a having a first capacitance $C_1$, and at least one second capacitor 300b having a second capacitance $C_2$ that is substantially equal to the first capacitance $C_1$. The at least one inductor 310 comprises at least one first inductor 310a having a first inductance $L_1$ and a first resistance $R_1$ (e.g., inductor loss) and at least one second inductor 310b having a second inductance $L_2$ that is substantially equal to the first inductance $L_1$ and a second resistance $R_2$ (e.g., inductor loss) that can be substantially equal to the first resistance $R_1$. The at least one first capacitor 300a is in series with the at least one first inductor 310a and with a first node of a load having a resistance $R_L$ due to the second circuitry 220. The at least one second capacitor 300b is in series with the at least one second inductor 310b and with a second node of the load having a resistance $R_L$ due to the second circuitry 220, the second node different from the first node. The "low resistor loaded" example series resonant tank circuit 232 of FIG. 3D.

In certain implementations in accordance with the third circuitry 230 of FIG. 3D, the first and second capacitances $C_1$, $C_2$ are sufficiently low (e.g., in a range of 100 pF to 1 nF) such that, during operation, the at least one capacitor 300 is a blocking capacitor for DC signals and stimulation AC signals. The values of the first and second capacitances $C_1$, $C_2$ and the first and second inductances $L_1$, $L_2$ can be set such that the power transfer coil 214 is in series resonance (e.g., unloaded) at a predetermined frequency (e.g., 5 MHz; 6.78 MHz). The load having a resistance $R_L$ due to the second circuitry 220 can be selected to allow series resonance with a predetermined Q of the series resonant tank circuit 232 (e.g., for battery charging and use of a voltage doubler). In certain implementations, the coil inductance $L_{coil}$ can be seen as a voltage source with mutual inductance $M_{21}$ that is much less than the first and second inductances $L_1$, $L_2$. In certain implementations, increasing the first and second inductances $L_1$, $L_2$ can be used to set the values of the first and second capacitances $C_1$, $C_2$ to practical values.

Figure 4:
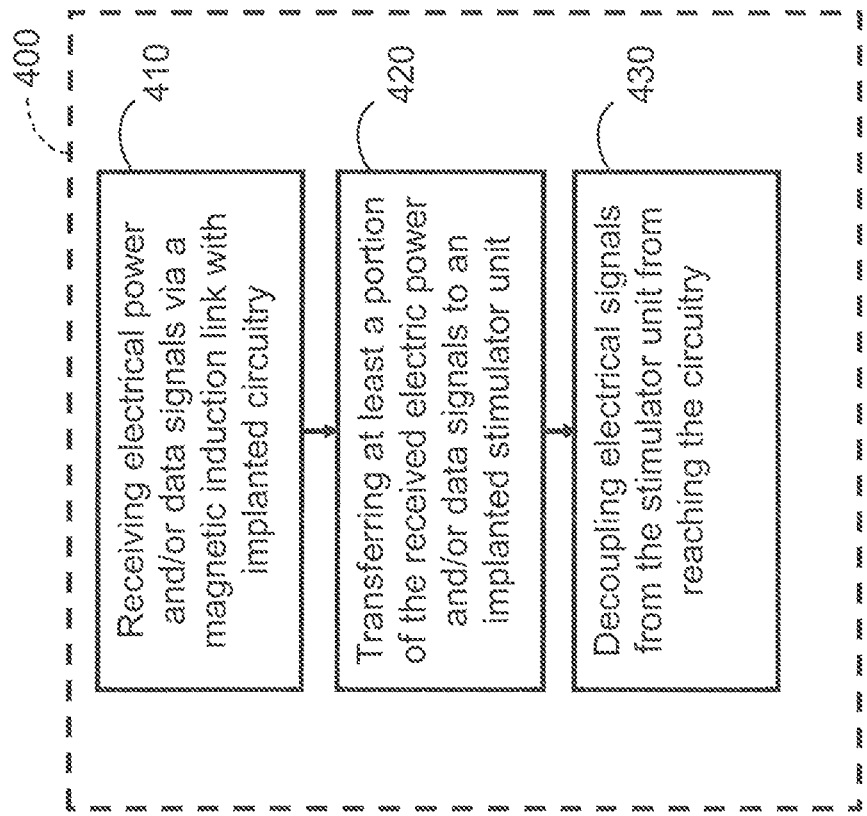
FIG. 4 is a flow diagram of an example method in accordance with certain implementations described herein.

FIG. 4 is a flow diagram of an example method 400 in accordance with certain implementations described herein. In an operational block 410, the method 400 comprises receiving electric power and/or data signals using circuitry implanted on or within a recipient's body. The electric power and/or data signals are received via a magnetic induction link between the circuitry and a device external to the recipient's body (e.g., a transcutaneous magnetic induction link). For example, the magnetic induction link can transfer electric power and/or data signals from an external portion of a medical device or system (e.g., an auditory or visual prosthesis system; cardiac pacemaker or defibrillator system) with the electric power and/or data signals received by an internal portion (e.g., implanted component) of the medical device or system. In certain implementations, the circuitry comprises an implanted microphone.

In an operational block 420, the method 400 further comprises transferring at least a portion of the received electrical power and/or data signals to an implanted stimulator unit configured to provide stimulation signals (e.g., stimulation pulses) to a portion of the recipient's body at a stimulation pulse rate. These stimulation signals can flow inside the tissue and can unintentionally be captured by the circuitry which could cause a degradation of the stimulation. The transferred electrical power and/or data signals have a first frequency above the stimulation pulse rate (e.g., the transferred electrical power and/or data signals operate within a first frequency range above the stimulation pulse rate). For example, the stimulation pulse rate can be less than or equal to 20 kHz, and the first frequency can be in a range greater than or equal to 1 MHz and/or less than 10 MHz. In certain implementations, the stimulator unit comprises two or more electrodes configured to provide neurostimulation signals to a portion of the recipient's body.

In an operational block 430, the method 400 further comprises decoupling electrical signals (e.g., electrical stimulation currents) from the stimulator unit from reaching the circuitry (e.g., stimulator unit), the decoupled electrical signals having a second frequency at or below the stimulation pulse rate. For example, the decoupled electrical signals can operate at a stimulation rate in a second frequency range different from the first frequency range of the transferred electrical power and/or data signals.

Although commonly used terms are used to describe the systems and methods of certain implementations for ease of understanding, these terms are used herein to have their broadest reasonable interpretations. Although various aspects of the disclosure are described with regard to illustrative examples and implementations, the disclosed examples and implementations should not be construed as limiting. Conditional language, such as, among others, "can," "could," "might," or "may," unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without user input or prompting, whether these features, elements and/or steps are included or are to be performed in any particular implementation. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

It is to be appreciated that the implementations disclosed herein are not mutually exclusive and may be combined with one another in various arrangements. In addition, although the disclosed methods and apparatuses have largely been described in the context of conventional cochlear implants, various implementations described herein can be incorporated in a variety of other suitable devices, methods, and contexts. More generally, as can be appreciated, certain implementations described herein can be used in a variety of implantable medical device contexts that can benefit from having at least a portion of the received power available for use by the implanted device during time periods in which the at least one power storage device of the implanted device unable to provide electrical power for operation of the implantable medical device.

Language of degree, as used herein, such as the terms "approximately," "about," "generally," and "substantially," represent a value, amount, or characteristic close to the stated value, amount, or characteristic that still performs a desired function or achieves a desired result. For example, the terms "approximately," "about," "generally," and "substantially" may refer to an amount that is within ±10% of, within ±5% of, within ±2% of, within ±1% of, or within ±0.1% of the stated amount. As another example, the terms "generally parallel" and "substantially parallel" refer to a value, amount, or characteristic that departs from exactly parallel by ±10 degrees, by ±5 degrees, by ±2 degrees, by ±1 degree, or by ±0.1 degree, and the terms "generally perpendicular" and "substantially perpendicular" refer to a value, amount, or characteristic that departs from exactly perpendicular by ±10 degrees, by ±5 degrees, by ±2 degrees, by ±1 degree, or by ±0.1 degree. The ranges disclosed herein also encompass any and all overlap, sub-ranges, and combinations thereof. Language such as "up to," "at least," "greater than," "less than," "between," and the like includes the number recited. As used herein, the meaning of "a," "an," and "said" includes plural reference unless the context clearly dictates otherwise. Also, as used in the description herein, the meaning of "in" includes "into" and "on," unless the context clearly dictates otherwise.

While the methods and systems are discussed herein in terms of elements labeled by ordinal adjectives (e.g., first, second, etc.), the ordinal adjective are used merely as labels to distinguish one element from another (e.g., one signal from another or one circuit from one another), and the ordinal adjective is not used to denote an order of these elements or of their use.

The invention described and claimed herein is not to be limited in scope by the specific example implementations herein disclosed, since these implementations are intended as illustrations, and not limitations, of several aspects of the invention. Any equivalent implementations are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example implementations disclosed herein, but should be defined only in accordance with the claims and their equivalents.

What is claimed is:

1. An apparatus comprising:
    first circuitry configured to be implanted on or within a recipient's body and to wirelessly receive electric power from a device external to the recipient's body;
    second circuitry configured to be implanted on or within the recipient's body and to provide stimulation signals to a portion of the recipient's body; and
    third circuitry configured to be implanted on or within the recipient's body, at least a portion of the first circuitry and at least a portion of the third circuitry forming a series resonant tank circuit configured to capacitively couple the second circuitry to the first circuitry while galvanically isolating the second circuitry from the first circuitry, so that at least a portion of the electric power is transferred from the first circuitry through the third circuitry to the second circuitry, wherein the third circuitry is further configured to allow pulsed electrical currents having a pulse rate greater than or equal to 20 kHz to transmit through the third circuitry from the second circuitry to the first circuitry while preventing pulsed electrical currents having a pulse rate less than 20 kHz from transmitting through the third circuitry from the second circuitry to the first circuitry.

2. The apparatus of claim 1, wherein the series resonant tank circuit comprises at least one inductor of the third circuitry, wherein the at least one inductor is in parallel with a load due to the second circuitry.

3. The apparatus of claim 1, wherein the series resonant tank circuit comprises at least one capacitor of the third circuitry.

4. The apparatus of claim 3, wherein the at least one capacitor comprises at least one first capacitor having a first capacitance and at least one second capacitor having a second capacitance substantially equal to the first capacitance, wherein the at least one first capacitor is in series with a first node of the at least one inductor and wherein the at least one second capacitor is in series with a second node of the at least one inductor.

5. The apparatus of claim 4, wherein the first capacitance is in a range of 100 pF to 1 nF and the at least one inductor has an inductance in a range of 0.2 micro Henry to 20 micro Henry.

6. The apparatus of claim 3, wherein the at least one capacitor comprises at least one first capacitor having a first capacitance, at least one second capacitor having a second capacitance substantially equal to the first capacitance, and at least one third capacitor in parallel with a load due to the second circuitry, wherein the at least one inductor is in parallel with the at least one third capacitor, wherein the at least one first capacitor is in series with a first node of the at least one inductor and wherein the at least one second capacitor is in series with a second node of the at least one inductor.

7. The apparatus of claim 1, wherein the first circuitry comprises an implant RF coil.

8. The apparatus of claim 1, wherein the first circuitry comprises at least one magnetic induction coil configured to transmit data signals between the first circuitry and the device external to the recipient's body.

9. The apparatus of claim 1, wherein the apparatus comprises a totally implantable cochlear implant system.

10. The apparatus of claim 1, wherein:
    the first circuitry comprises a magnetic induction coil configured to wirelessly receive the electric power from the device external to the recipient's body; and
    the second circuitry is capacitively coupled to the first circuitry and is configured to receive at least a portion of the electric power from the first circuitry, and the series resonant tank circuit is configured to provide an isolation impedance between the first and second circuitry sufficient to block the stimulation signals from the first circuitry.

11. The apparatus of claim 10, wherein the series resonant tank circuit comprises a first capacitor and a second capacitor having substantially equal capacitances.

12. The apparatus of claim 10, wherein the series resonant tank circuit comprises at least one inductor configured to increase the isolation impedance between the first circuitry and the second circuitry to be greater than an isolation impedance between the first circuitry and the second circuitry without the at least one inductor.

13. The apparatus of claim 10, wherein the first circuitry further comprises a microphone implanted within the recipient's body.

14. The apparatus of claim 10, wherein the second circuitry comprises a stimulator unit of an auditory prosthesis, the stimulator unit configured to generate the stimulation signals based on data signals received from the first circuitry.

15. The apparatus of claim 2, wherein the first circuitry is configured to receive the electric power from the device via a transcutaneous magnetic induction link.

16. The apparatus of claim 2, wherein the second circuitry comprises two or more electrodes configured to provide neurostimulation signals to a portion of the recipient's body.

17. The apparatus of claim 2, wherein the apparatus and the device are portions of an implantable medical system comprising an auditory prosthesis system, a visual prosthesis system, cardiac pacemaker system, or a cardiac defibrillator system.

18. The apparatus of claim 1, wherein the first circuitry is configured to receive the electric power from the device via a transcutaneous magnetic induction link.

19. The apparatus of claim 1, wherein the second circuitry comprises two or more electrodes configured to provide neurostimulation signals to a portion of the recipient's body.

20. The apparatus of claim 1, wherein the apparatus and the device are portions of an implantable medical system comprising an auditory prosthesis system, a visual prosthesis system, cardiac pacemaker system, or a cardiac defibrillator system.

21. An apparatus comprising:
first circuitry configured to be implanted on or within a recipient's body and to wirelessly receive electric power from a device external to the recipient's body;
second circuitry configured to be implanted on or within the recipient's body and to provide stimulation signals to a portion of the recipient's body; and
third circuitry configured to be implanted on or within the recipient's body, at least a portion of the first circuitry and at least a portion of the third circuitry forming a series resonant tank circuit configured to capacitively couple the second circuitry to the first circuitry while galvanically isolating the second circuitry from the first circuitry, so that at least a portion of the electric power is transferred from the first circuitry through the third circuitry to the second circuitry, wherein the series resonant tank circuit comprises at least one capacitor of the third circuitry and at least one inductor of the third circuitry, wherein the at least one capacitor comprises at least one first capacitor having a first capacitance, at least one second capacitor having a second capacitance substantially equal to the first capacitance, and at least one third capacitor in parallel with a load due to the second circuitry, wherein the at least one inductor comprises at least one first inductor having a first inductance and at least one second inductor having a second inductance substantially equal to the first inductance, wherein the at least one first capacitor is in series with the at least one first inductor and with a first node of the at least one third capacitor, and wherein the at least one second capacitor is in series with the at least one second inductor and with a second node of the at least one third capacitor.

22. The apparatus of claim 21, wherein the first circuitry is configured to receive the electric power from the device via a transcutaneous magnetic induction link.

23. The apparatus of claim 21, wherein the second circuitry comprises two or more electrodes configured to provide neurostimulation signals to a portion of the recipient's body.

24. The apparatus of claim 21, wherein the apparatus and the device are portions of an implantable medical system comprising an auditory prosthesis system, a visual prosthesis system, cardiac pacemaker system, or a cardiac defibrillator system.

25. An apparatus comprising:
first circuitry configured to be implanted on or within a recipient's body and to wirelessly receive electric power from a device external to the recipient's body;
second circuitry configured to be implanted on or within the recipient's body and to provide stimulation signals to a portion of the recipient's body; and
third circuitry configured to be implanted on or within the recipient's body, at least a portion of the first circuitry and at least a portion of the third circuitry forming a series resonant tank circuit configured to capacitively couple the second circuitry to the first circuitry while galvanically isolating the second circuitry from the first circuitry, so that at least a portion of the electric power is transferred from the first circuitry through the third circuitry to the second circuitry, wherein the series resonant tank circuit comprises at least one capacitor of the third circuitry and at least one inductor of the third circuitry, wherein the at least one capacitor comprises at least one first capacitor having a first capacitance and at least one second capacitor having a second capacitance substantially equal to the first capacitance, wherein the at least one inductor comprises at least one first inductor having a first inductance and at least one second inductor having a second inductance substantially equal to the first inductance, wherein the at least one first capacitor is in series with the at least one first inductor and with a first node of a load due to the second circuitry, and wherein the at least one second capacitor is in series with the at least one second inductor and with a second node of the load due to the second circuitry.

26. The apparatus of claim 25, wherein the first circuitry is configured to receive the electric power from the device via a transcutaneous magnetic induction link.

27. The apparatus of claim 25, wherein the second circuitry comprises two or more electrodes configured to provide neurostimulation signals to a portion of the recipient's body.

28. The apparatus of claim 25, wherein the apparatus and the device are portions of an implantable medical system comprising an auditory prosthesis system, a visual prosthesis system, cardiac pacemaker system, or a cardiac defibrillator system.

* * * * *